United States Patent [19]
Co

[11] 3,935,857
[45] Feb. 3, 1976

[54] CARDIAC CATHETER
[76] Inventor: Eddy D. Co, 3032 W. Iona Terrace, Milwaukee, Wis. 53221
[22] Filed: July 31, 1974
[21] Appl. No.: 493,389

[52] U.S. Cl. ............................... 128/2.05; 128/348
[51] Int. Cl.² ......................................... A61M 25/00
[58] Field of Search ....... 128/2 A, 2 R, 2.05 R, 348, 128/350 R

[56] References Cited
UNITED STATES PATENTS
3,485,234 12/1969 Stevens ........................... 128/348 X
3,612,038 10/1971 Halligan ........................... 128/348 X OTHER PUBLICATIONS
Bourassa –Angiology –Vol. 22, No. 6, June 1971, pp. 320-331 128-348.
USCI Catalogue –1967–p. 12.

Primary Examiner—Dalton L. Truluck
Attorney, Agent, or Firm—Andrus, Sceales, Starke & Sawall

[57] ABSTRACT

A catheter for cardiac studies which is made of relatively high torque plastic material and which is formed with a pair of straight legs joined by a continuous curve and wherein the said legs are disposed at an angle of 85°. The curve is such that the straight line distance from its midpoint to the intersection of the imaginary inward extensions of said legs is ¼ the chordal straight line distance between the two points where the said straight legs merge into said curve.

5 Claims, 9 Drawing Figures

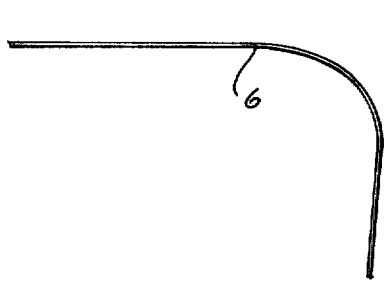
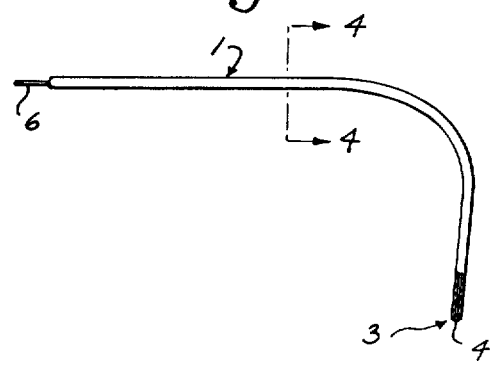
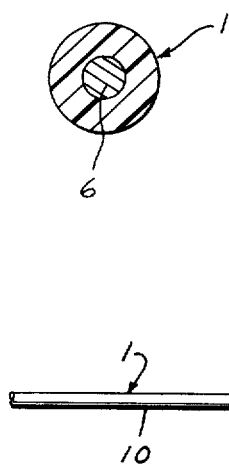
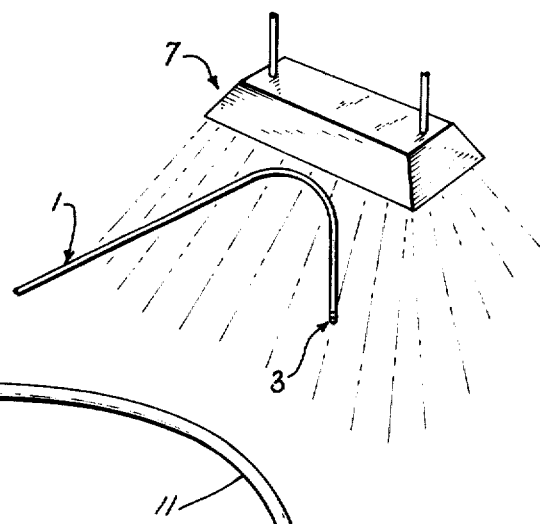
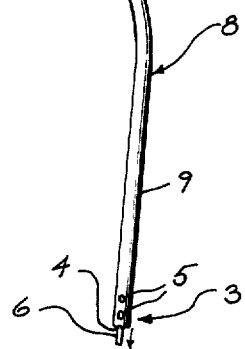

3,935,857

CARDIAC CATHETER

BACKGROUND AND SUMMARY OF THE INVENTION

This invention relates to a cardiac catheter, and more particularly to a catheter for use in studying the action and condition of the heart. Cardiac catheters are used for making X-ray motion picture film in such procedures as coronary arteriography, ventricular angiography, vein graft studies and pulmonary angiograms. Both sides of the heart may be studied.

In coronary arteriography, the catheter is inserted into an artery in an arm or leg and passed therethrough into the aorta and hence into contact with the ostium of the respective coronary artery within the heart. A suitable dye is pressure injected through the catheter into the working heart and X-ray photographs may then be taken for the purpose of attempting to locate any abnormality in the heart structure or function. Since the patient is subjected to strong X-rays, on the order of 80-90 K.V., during the taking of motion picture film, it is imperative that the procedure take as little time as possible, while obtaining all of the required visual information.

Heretofore, various types of catheters have been developed to accomplish the indicated task. However, to the knowledge of the present inventor, all of them have been subject to certain disadvantages which have not only lengthened the time for the various procedures, but have also subjected the patient to possible dangers. Some catheters have been constructed of relatively flexible plastic which, while easy to insert into the heart, will soften due to body heat and lose the desired position at the ostium. Others have been so rigid that they are hard to manipulate adjacent the heart. Perhaps of greatest importance is the tendency of prior catheters to miss making proper contact with the coronary artery ostium during insertion, or to fall or slip from the ostium almost immediately upon contact therewith. This latter problem has previously been partially solved by making different shaped catheters, one for the right ostium and one for the left. However, in order to inject dye into both coronary arteries and thus obtain a complete study of both sides of the heart, it has been necessary to remove a right catheter completely from the body, replace it with a left catheter and then re-insert the apparatus. This causes a doubling of the exposure to X-rays and adds trauma to the artery.

There has long been a need for a cardiac catheter which will make quick and certain contact with the artery ostium, without the danger of its falling out; as well as a single catheter which is usable for both sides of the heart. To the knowledge of the present inventor, this need has not previously been met.

The present invention is based on a solution to the aforementioned problems and the filling of the aforementioned need by the development of a catheter of suitable material which is shaped in a particular manner. Briefly in accordance with the invention, a catheter of relatively high torque plastic material is formed with a pair of straight legs joined by a continuous curve and wherein the said legs are disposed at an angle of 85°. The curve is such that the straight line distance from its midpoint to the intersection of the imaginary inward extensions of said legs is ¼ the chordal straight line distance between the two points where the said straight legs merge into said curve.

BRIEF DESCRIPTION OF THE DRAWINGS

The accompanying drawings illustrate the best mode presently contemplated by the inventor for carrying out the invention.

In the drawings:

FIG. 1 is a front elevation of the straight end portion of a catheter tube from which the catheter of the invention is constructed, and with a portion thereof broken away;

FIG. 2 is a side elevation of a forming wire used in shaping the catheter tube end portion;

FIG. 3 is a side elevation of the forming wire assembled into the catheter tube;

FIG. 4 is an enlarged section taken on on line 4--4 of FIG. 3;

FIG. 5 is a schematic view showing the permament forming of the catheter of the invention;

FIG. 6 is a side elevation of the formed catheter end portion, and schematically showing removal of the forming wire;

DESCRIPTION OF THE PREFERRED EMBODIMENT

Figure 7:
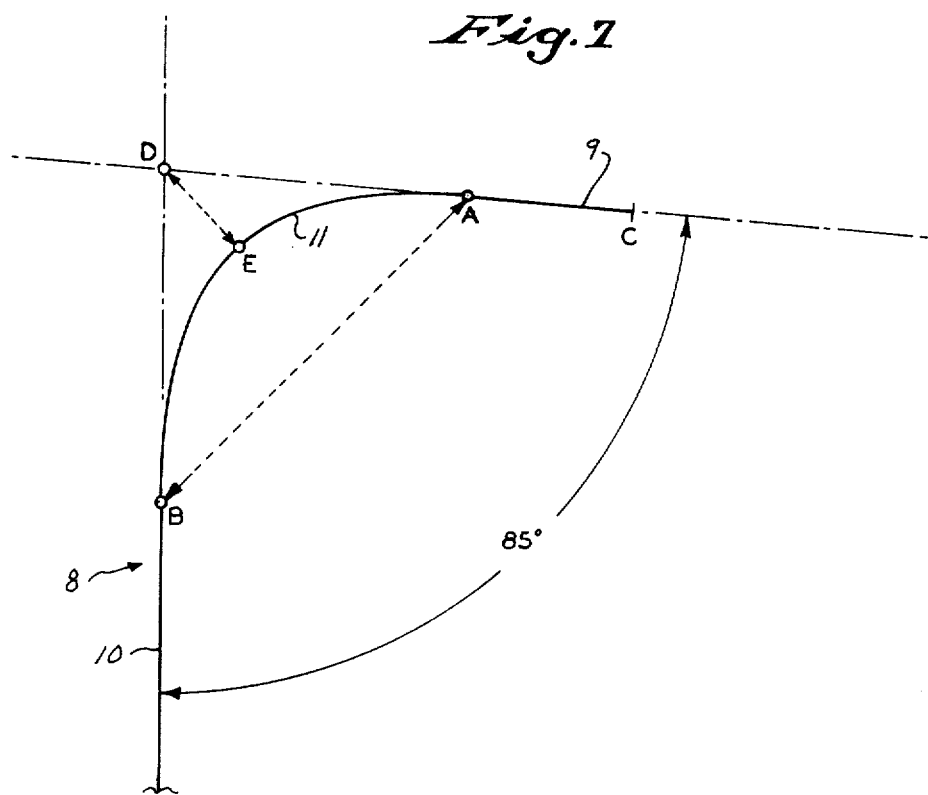
FIG. 7 is a side elevation of the formed catheter end portion and showing the geometric relationship of the elements thereof.

As shown in FIG. 1 of the drawings, the catheter of the invention is formed from a length of straight tubing 1. Since the total length necessary for insertion through an artery of vein and into the heart is substantial, and since the invention is primarily concerned with the heart-engaging catheter end, the tubing is shown as broken off at 2. The outer end portion 3 of tubing 1 is shown as having an end opening 4 and a plurality of side openings 5 for pressurized distribution of dye into the heart.

Tubing 1 is contemplated as being formed of lightweight flexible plastic of a substantially constant thickness throughout. The material is preferably of braided polyurethane of relatively high torque characteristics and which is not thermoplastic but rather shape stable in the range of body temperatures encountered.

It is desired that tubing 1 be formed into a catheter having the required dimensional and shape characteristics. For this purpose, and as best shown in FIGS. 2–6, a short forming wire 6 is provided and which has the substantial identical geometry as the finished catheter. Wire 6 is inserted into tubing 1 at its end (FIG. 3) and the assembly is suitably heated, as by the heat lamp 7 (FIG. 5) so that tubing 1 is re-shaped and permanently sets into the final desired shape of formed catheter 8 (FIG. 6). Wire 6 is then removed.

Referring to FIGS. 6 and 7, catheter 8 is of a very special configuration and comprises a pair of linear or straight legs 9, 10 which are joined by a continuously curved central portion 11. Legs 9 and 10 merge into curved portion 11 at points A and B respectively. Inner leg 10 forms a portion of the extended tubing 1, while outer leg 9 is shorter and of finite length, terminating in the end of the catheter, as at point C.

It has been found that in order for the catheter tip to enter the coronary artery ostium of an adult heart, the minimum length of outer leg 9 (distance AC) must be 14 mm (± 2 mm). Longer outer legs may be utilized in the case of larger heart sizes.

In accordance with the invention, legs 9 and 10 must be disposed at an acute angle of 85° (± 3°). As shown in FIG. 7, the imaginary extensions of the legs intersect at D to form the angle.

Curved portion 11 is shown as being of almost infinite radius at merging points A and B and gradually decreases in radius inwardly from each point to its central point E. In accordance with the invention, the nature of curve 11 is such that the straight line distance from the curve's midpoint to the intersection of the imaginary inward extensions of legs 9 and 10 (distance DE) is at or very close to ¼ the chordal straight line distance between the two leg-curve merge points (distance AB).

It has been found that in order to obtain the desired results, the following dimensions must remain the same (± 2 mm) for all catheters constructed in accordance with the invention: AD = 27 mm, BD = 27 mm and AB = 36 mm. Thus the line DE will be 9 mm; or $$\frac{DE}{AB} = \frac{9}{36} = \frac{1}{4}.$$

Figure 8:
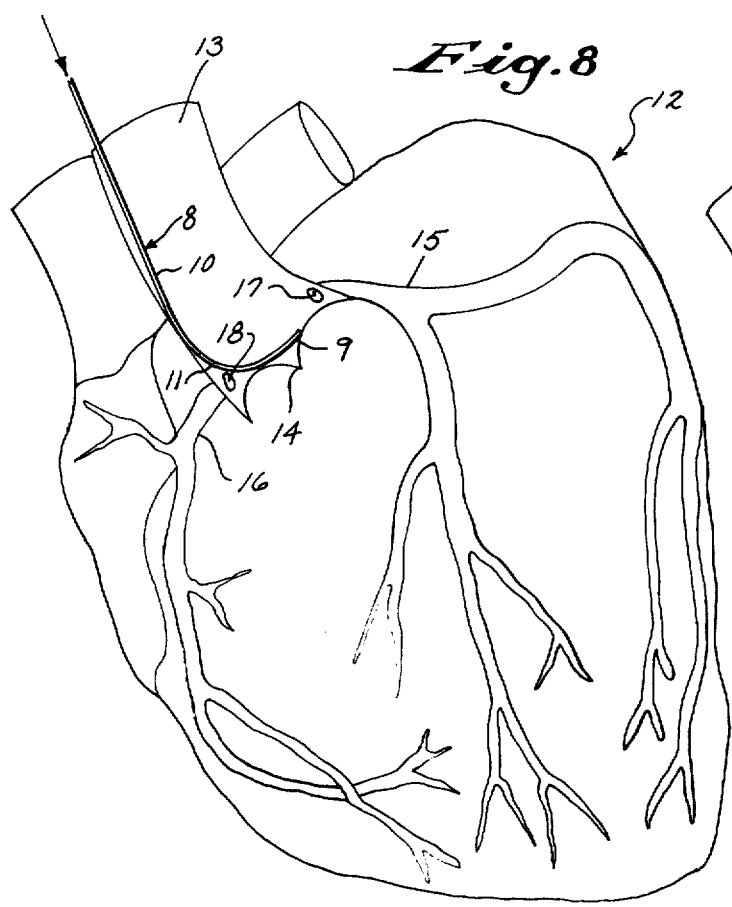
FIG. 8 is a somewhat schematic view of an adult human heart and showing preliminary insertion of the catheter through the aorta.

FIG. 8 illustrates schematically an adult human heart 12 in what would be considered a left anterior oblique view. Heart 12 includes an aorta 13 which extends into a chamber containing the major heart valve 14 at its lower end and which permits entry of blood into the heart interior. Left and right coronary arteries 15, 16 form a part of the heart and have respective ostiums 17, 18 which provide communication with the said chamber above valve 14. Ostiums 17 and 18 are generally opposed across aorta 13 and are at approximately the same level, although they appear to be at slightly different levels in the oblique view type drawings.

Figure 9:
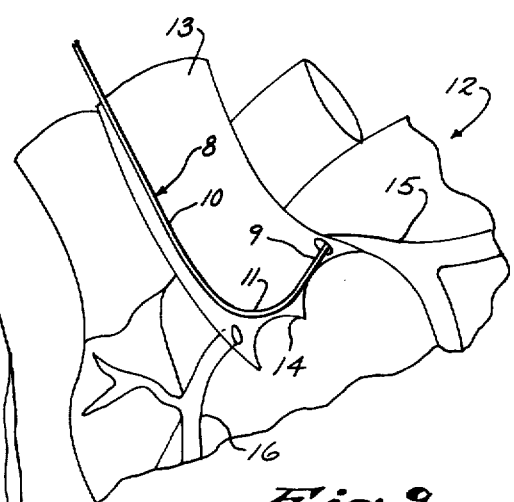
FIG. 9 is a fragmentary view of a portion of the heart of FIG. 8 and showing the end of the catheter in position in the left coronary artery ostium.

During the procedure described heretofore, catheter 8 and its outward tubular extension is inserted into the patient and moved into and through aorta 13 until it engages valve 14. This procedure is observed at all times by X-ray screen or the like. After initial engagement with valve 14, as shown in FIG. 8, the catheter end will slide along the valve and will loop upwardly until the catheter tip firmly and accurately enters an ostium, such as left artery ostium 17 as shown in FIG. 9. Injection of dye and X-ray studies of the heart may then be made. While catheter 8 may flex somewhat during insertion through the aorta, it will spring back into its pre-formed shape as it engages valve 14 and enters the ostium.

After one side is studied, the catheter may be removed from ostium 17 by pulling slightly upwardly on the tube, the tube twisted by approximately 180° and then the catheter lowered against valve 14 so that the catheter tip loops up and then enters right ostium 18.

The inventor has found that with the specific physical and geometric structure previously described, the catheter tip will easily engage the ostium at the proper point and will stay firmly in place and not fall out as with prior devices. Furthermore, a single catheter will service both right and left sides, and it will not lose its desirable flexure characteristics when subjected to internal body heat.

Various modes of carrying out the invention are contemplated as being within the scope of the following claims particularly pointing out and distinctly claiming the subject matter which is regarded as the invention.

I claim:
1. A catheter for insertion through the aorta and into tip engagement with a coronary artery ostium of a human heart, said catheter comprising:
   a. a preformed tubular body of relatively high torque flexible plastic and of substantially constant thickness throughout,
   b. said body having straight inner and outer legs joined by a continuously curved central portion and with said outer leg forming the tip of the catheter,
   c. said continuously curved central portion being of substantially infinite radius at its points of merger with said legs and gradually decreasing in radius inwardly from said points toward its central point,
   d. said legs being disposed at an angle of substantially 85° to each other,
   e. the straight line distance from said curved portion's midpoint to the intersection of the imaginary inward extensions of said legs (FIG. 7, line D-E) being about ¼ the chordal straight line distance between the points of merger of said legs with said curved portion (FIG. 7, line A-B),
   f. the construction being such that said catheter is usable for tip engagement with either the left or right artery ostium and without falling therefrom during photographic heart studies.

2. The catheter of claim 1 in which said outer leg portion is shorter than said inner leg portion.

3. The catheter of claim 2 wherein distance DE is about 9 mm and distance AB is about 36 mm.

4. The catheter of claim 3 wherein the minimum length of said outer leg (FIG. 7, line A-C) is 14 mm (± 2 mm); and the distances AD and BD of FIG. 7 are 27 mm (± 2 mm).

5. The catheter of claim 4 in which said catheter is made of material which is shape stable in the range of internal body temperatures.

* * * * *